United States Patent [19]
Jahn et al.

[11] Patent Number: 6,145,390
[45] Date of Patent: Nov. 14, 2000

[54] FLAT AND ELONGATED DEVICE FOR MEASURING PARTICLE SIZES

[75] Inventors: David W. Jahn, Cincinnati; Patrick A. Jacomet, Troy, both of Ohio

[73] Assignee: Martin Marietta Materials, Inc., Raleigh, N.C.

[21] Appl. No.: 09/233,935

[22] Filed: Jan. 20, 1999

Related U.S. Application Data

[60] Provisional application No. 60/071,858, Jan. 20, 1998, and provisional application No. 60/109,593, Nov. 23, 1998.

[51] Int. Cl.[7] .................................................. G01N 15/00
[52] U.S. Cl. ...................................... 73/865.5; 73/863.23
[58] Field of Search ............................... 73/863.23, 865.5

[56] References Cited

U.S. PATENT DOCUMENTS

| | | | |
|---|---|---|---|
| 3,678,759 | 7/1972 | Schneeberger | 73/865.5 |
| 3,719,089 | 3/1973 | Kelsall et al. | 73/865.5 |
| 3,739,180 | 6/1973 | Carlson | 73/865.5 |
| 5,578,771 | 11/1996 | Karhu | 73/865.5 |

*Primary Examiner*—Harshad Patel
*Attorney, Agent, or Firm*—McDermott, Will & Emery

[57] ABSTRACT

An apparatus for measuring dimensions of particles includes a base. At least three fixed posts are mounted to the base. A swinging arm is pivotally mounted to the base about a pivot point. The swinging arm has a first section mated with a first of the at least three fixed posts, a second arm mated with a second and a third of the at least three fixed posts, and a third section connecting the first and second sections. The first section has a first length and the second section has a second length. A first opening is formed when the first section and the first fixed post are not in contact. Second and third openings are formed when the second section does not contact the second and third fixed posts.

4 Claims, 8 Drawing Sheets

INDIANA #8 LIMESTONE
FLAT AND ELONGATED RATIO AT 3:1
(MAXIMUM TO MINIMUM)

FLAT AND ELONGATED DEVICE FOR MEASURING PARTICLE SIZES

This application claims the benefit of U.S. Provisional Application Ser. Nos. 60/071,858, filed Jan. 20, 1998 and 60/109,593 filed Nov. 23, 1998.

FIELD OF THE INVENTION

The present invention generally relates to an apparatus and method for measuring the dimensions of particles in order to determine whether the particles meet product specifications.

BACKGROUND OF THE INVENTION

Aggregates, i.e., crushed stone, sand and gravel, are the most fundamental components used in construction. Approximately fifty percent of aggregates are shipped for highway construction, either as a road base or a primary component of asphalt and concrete. Aggregates are also used in commercial and residential construction as a base for foundations, concrete and parking lots. Other uses for aggregates, some of which require a high-quality, chemical-grade limestone, include: riprap for erosion control; railroad ballast; flux stone; filter stone; agricultural limestone; production of cement and lime; desulfurization; acid neutralization; animal feed supplements; and plastic and paint fillers. Regardless of the use, the production requirements of stone aggregates are complex because the material must be crushed to multiple sizes, often washed to remove fines and impurities, and sometimes processed further in order to meet the specification for its intended use. Without the physical and chemical properties provided by aggregates, modem construction materials and methods, as well as a multitude of industrial products, would not be possible.

Product requirements often dictate the percentages of flat particles, elongated particles or flat and elongated particles in coarse aggregates, i.e., crushed stone or gravel that will not, when dry, pass through a sieve with specified diameter holes. For example, flat or elongated particles of aggregates for some construction uses may interfere with consolidation and result in harsh, difficult to place materials. Flat particles are defined as those particles that exceed a specified ratio of width to thickness. For example, if the ratio is 3:1, the width cannot exceed three times the thickness. (A specification will give a percentage and then the ratio, such as 20% 3:1, meaning a sample fails the specification if more than 20% of the particles (individual pieces) tested have ratios that exceed 3:1.) Elongated particles are defined as those particles that exceed a specified ratio of length to width. Flat or elongated particles are defined as those particles of aggregate having a ratio of width to thickness or length to width greater than a specified value. Flat and elongated particles of aggregate are defined to be those particles having a ratio of length to thickness greater than a specified value.

Sieve size is the size of an opening that a particle can pass through. The specification may require that the amount of particles passing through the opening be determined ("percent passing"). Or, the specification may require that the percent of the sample that does not pass through a specified opening be determined ("percent retained").

Aggregate size refers to a description of the product based on how much of the product passes (or could be given as how much is "retained on") a specified number of sieve sizes, or openings. For example, an ASTM (American Society of Testing and Materials) #57, a typical product used in concrete and asphalt construction, is described by using sieve sizes as follows (sieve sizes are square openings):

| Sieve Size | % Passing | |
|---|---|---|
| 1 ½ inches | 100% | 100% of the sample must pass through an 1 ½ inch square opening |
| 1 inch | 95–100% | Between 95 and 100% of the particles must be smaller than 1 inch |
| ½ | 25–60% | Between 25 and 60% of the particles must be smaller than ½ inch |
| #4 | 0–10% | #4 is close to ¼ inch opening |
| #8 | 0–5% | #8 is close to ⅛ inch opening |

Figure 1:
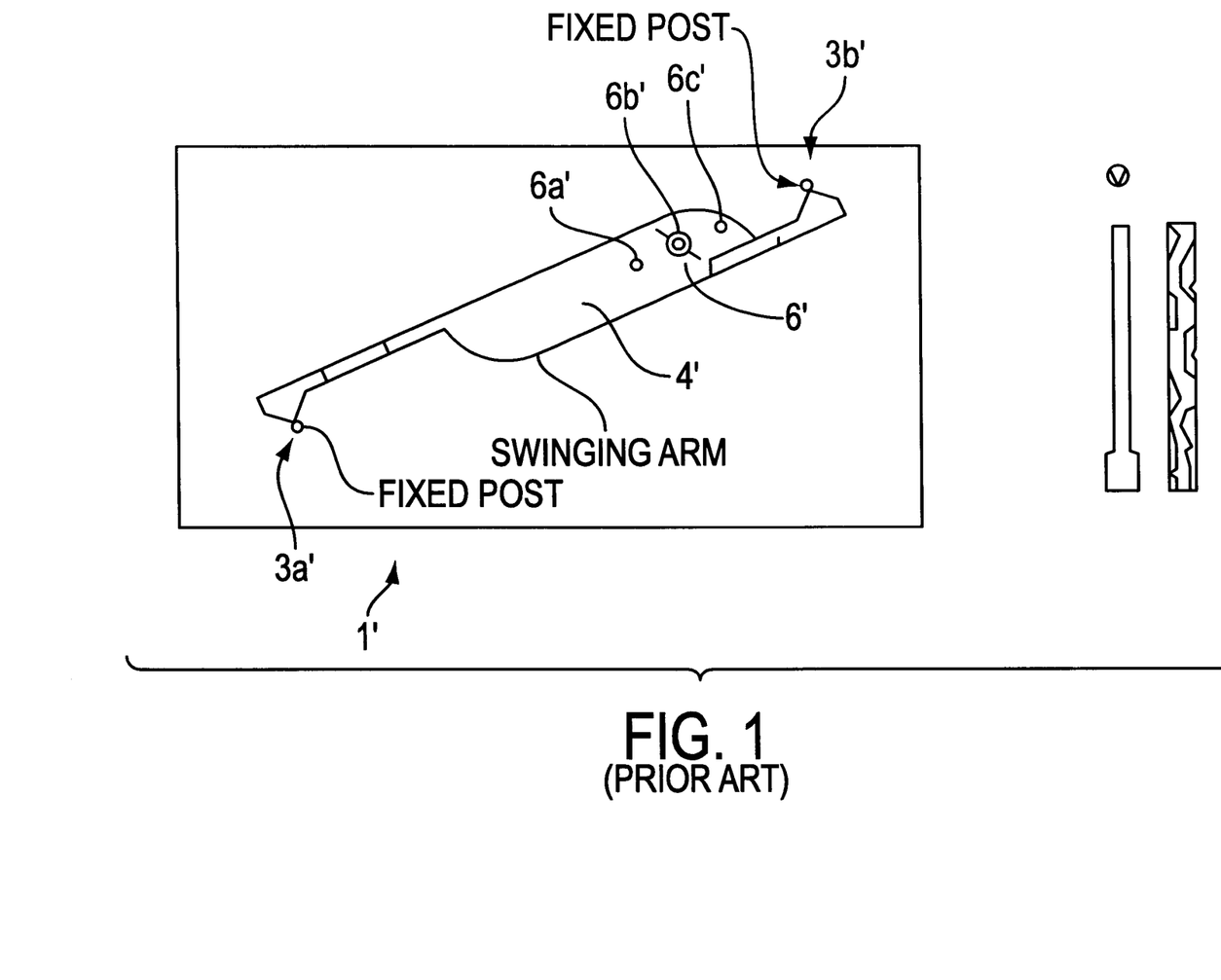
FIG. 1 is a schematic showing a view of a prior art device for measuring the dimensions of particles.

Prior apparatus and methods for measuring individual particles of aggregate of specific sieve size to determine the ratio of width to thickness, length to width, or length to thickness include that disclosed in *Standard Test Method for Flat Particles, Elongated Particles, or Flat and Elongated Particles in Coarse Aggregate,* ASTM Designation D 4791-95, the entire contents of which are incorporated herein by reference. Referring to prior art FIG. 1, which is a schematic of a proportional caliper device 1' that consists of a base plate (not shown) with two fixed posts 3a' and 3b' and a swinging arm 4' mounted between them so that the openings (larger opening, not shown) and (smaller opening, not shown) between the swinging arm 4' and the two fixed posts 3a' and 3b' maintain a constant ratio. The axis position 6' can be adjusted to provide the desired ratio of opening dimensions. FIG. 1 illustrates a device on which ratios of 1:2, 1:3 and 1:5 may be set (6a', 6b' and 6c', respectively). The axis position 6' must be moved to change the ratio being measured. A complete re-measuring of the particle under test each time a new ratio is selected (axis position 6' is moved) is thus required. The device disclosed in FIG. 1 is capable of measuring only one ratio at a time and is therefore capable of only determining whether a particle is larger or smaller than a single ratio.

Figure 2:
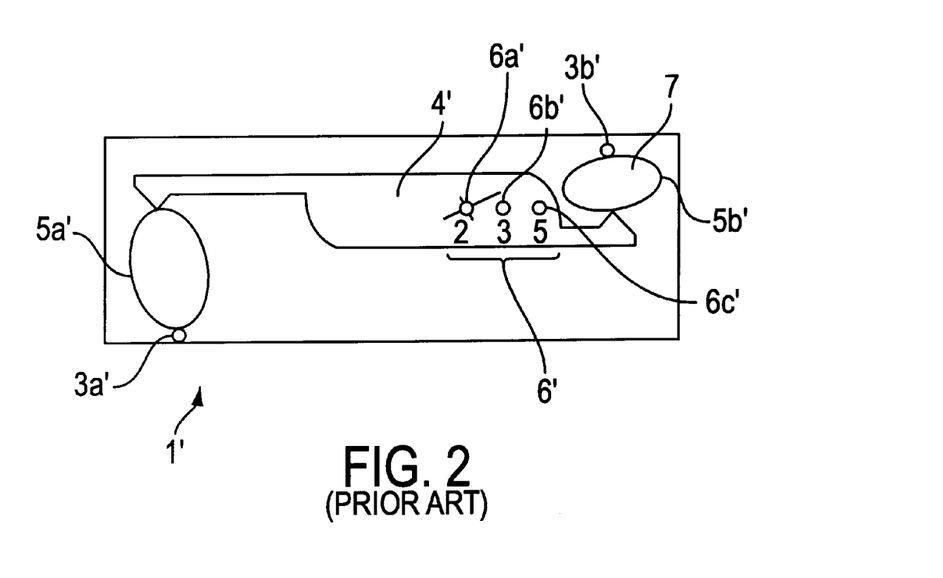
FIG. 2 is a schematic showing the use of the prior art device of FIG. 1 to measure the elongation of particles.
Figure 3:
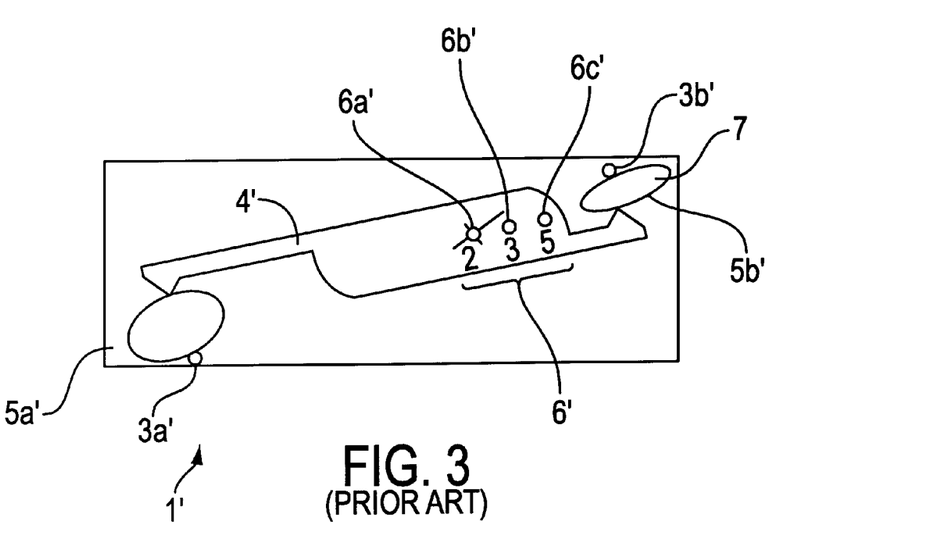
FIG. 3 is a schematic showing the use of the prior art device of FIG. 1 to measure the flatness of particles.

Referring to FIG. 2 and FIG. 3, FIG. 2 and FIG. 3 are schematics showing the use of the prior art device of FIG. 1 to (1) measure the elongation of aggregate particles and (2) measure the flatness of aggregate particles, respectively. A sample of aggregate particles is prepared pursuant to the methods disclosed in D 4791-95. The ratios of particle dimensions are then determined using the proportional caliper device 1' of FIG. 1. The determination of ratios of particle dimensions may be reported by mass or by particle count. If reported by mass, the sample is first dried at a temperature of about 230° F. (approximately 110° C.) to ensure constant mass. The sample of coarse aggregate to be tested is sieved and each size fraction larger than the 9.5-mm (⅜-in.) sieve present in the amount of 10% or more of the original sample is reduced until approximately 100 particles are obtained. The proportional caliper device 1' is then positioned at the specified ratio and the particle test is run as follows: Flat Particle Test (FIG. 3)—the larger opening 5a' equal to the particle width is set. The particle 7 is flat if the thickness can be placed in the smaller opening 5b'. Elongated Particle Test (FIG. 2)—the larger opening 5a' equal to the particle length is set. The particle 7 is elongated if the width can be placed within the smaller opening 5b'. After the particles have been classified into groups, the proportion of the sample in each group is determined by either count or by mass, as required. Flat and Elongated Particle Test—each of the particles in each size fraction is tested and placed in one of two groups: (1) flat and elongated or (2) not flat and elongated. The proportional caliper device 1' is set at the desired ratio as shown in FIG. 2. The larger opening 5a' equal to the particle length is set. The particle 7 is flat and elongated if the thickness can be placed in the smaller opening 5b'. After the particles have been classified into groups, the proportion of the sample in each group is determined by either count or mass as required. The percentage of flat and elongated particles to the nearest 1% for each sieve size greater than 9.5 mm (⅜-in.) is calculated.

Occasionally, AASHTO (American Association of State Highway Transportation Officials) changes specifications from one ratio requirement to another and many states have ratio requirements that differ from the AASHTO ratios to determine flat and elongated particle shape failures. The measurements to determine the relative proportions of a sample of particles, which are generally carried out on a sample of 100 particles or more, are conducted on one aggregate particle at a time. The ability to measure two or more ratios simultaneously would save time and effort on an already tedious procedure.

There therefore remains a need for better apparatus and methods that are capable of measuring the dimensions of particles in order to determine whether the particles meet product specifications.

SUMMARY OF THE INVENTION

The apparatus and method of the present invention provide a rapid and efficient means for checking compliance of aggregate particles with specifications that limit the percentages of flat and/or elongated particles and/or the determination of the relative shape characteristics of coarse aggregates. In particular, the apparatus and method of the present invention permit the measurement of two or more, for example, two to five ratios (e.g., less than 2:1, between 2:1 and 3:1, between 3:1 and 4:1, between 4:1 and 5:1 and greater than 5:1) at one time, thus saving the technician significant time and effort.

The apparatus and method of the present invention permit easy modification of tests to meet changes in standards and various state ratio requirements.

Accordingly it is an object of the present invention to provide an apparatus and method for measuring the dimensions of particles in order to determine whether the particles meet product specifications.

It is another object of the present invention to provide an apparatus and method for measuring the dimensions of particles so as to reduce the time required to make such measurements.

It is a further object of the present invention to provide a simple and efficient apparatus and method for measuring the dimensions of particles.

In accordance with the above and other objects, the inventive apparatus comprises:

a base;

three or more fixed posts mounted to the base;

a swinging arm mounted to the base, wherein the swinging arm has a first end, wherein the first end mates with a first fixed point, a second end wherein the second end mates with a second fixed point, and a center connecting the first end and the second end, wherein the swinging arm is mounted to the base so as to permit movement thereof around a pivot point, wherein the first end has a length $L_1$ that is less than a length $L_2$ of the second end.

The inventive method involves:

measuring dimensions of particles, wherein two or more ratios of a particle are measured simultaneously.

Additional objects and attendant advantages of the present invention will be set forth in the description and examples that follow, or may be learned from using the apparatus or practicing the method of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further objects and attendant advantages, will best be understood by reference to the following detailed description, taken in conjunction with the accompanying drawings.

BRIEF DESCRIPTION OF THE DRAWINGS

FIG. 9 is a bar graph showing the calculated results (calculated in accordance with the second embodiment of the invention) for the same sample of Indiana #8 Limestone as used in FIG. 7 at the following ratios: (a) between 1:1 and 2:1, (b) between 2:1 and 3:1, (c) between 3:1 and 4:1, and (d) between 4:1 and 5:1. FIG. 9 is similar to FIG. 8. However, FIG. 9 also shows the percent ratios found in each group of the particle sizes found within the sample of Indiana #8 Limestone.

DETAILED DESCRIPTION OF THE INVENTION

All patents, patent applications and literatures that may be cited in this description are incorporated herein by reference in their entirety.

As an aid to understanding, but without being limited thereby, the present invention is based on the discovery of a mechanism that permits the gauging of particles at more than one ratio simultaneously.

Figure 4A:
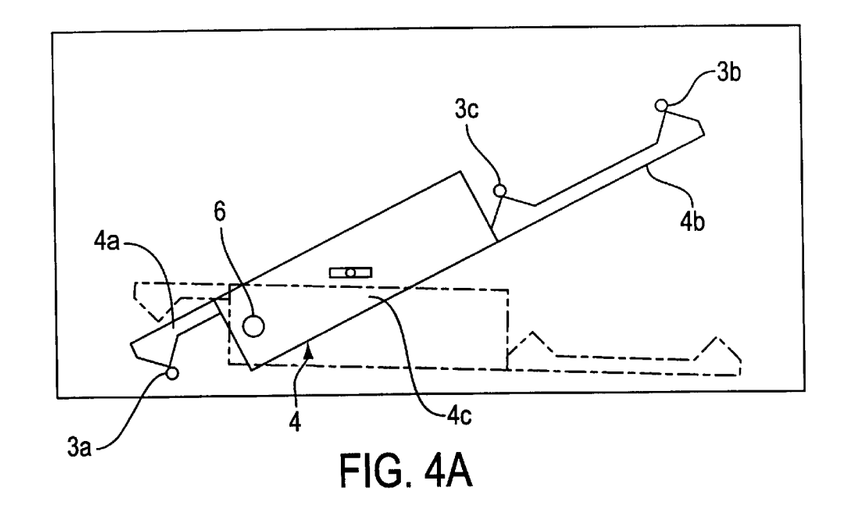
FIGS. 4A, 4B and 4C are schematics showing views of an apparatus for measuring the dimensions of particles in accordance with the present invention, wherein two measurements, i.e., 5:1 and 3:1, may be carried out simultaneously.
Figure 4B:
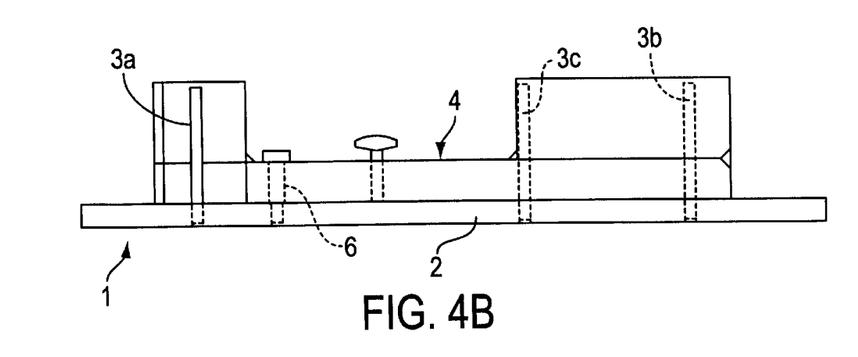
Figure 4C:
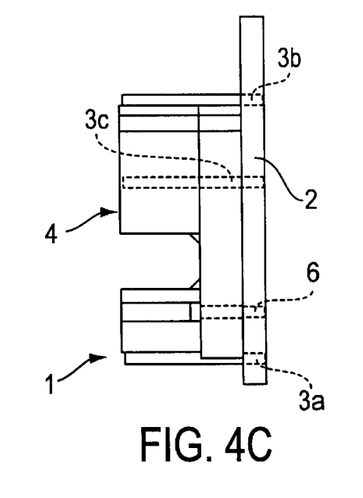

Referring to FIGS. 4A, 4B and 4C, there is shown an apparatus for measuring the dimensions of particles in accordance with a first embodiment of the present invention. The apparatus contains a base plate 2 with three fixed posts, 3a, 3b and 3c, and a swinging arm 4 mounted between the length of the first fixed post 3a and the third fixed post 3b. As disclosed herein, the apparatus may have three or more fixed posts and be within the scope of the present invention. The swinging arm 4 is mounted on the base plate 2 so as to permit movement of the swinging arm 4 around a pivot point 6. The swinging arm 4 contains three sections, 4a, 4b and 4c. The first section 4a mates the first fixed post 3a. The second section 4b mates the second fixed post 3c and the third 3b fixed post. The first section 4a has a length $L_1$ that is less than the length $L_2$ of the second section 4b. The third section 4c connects the first section 4a and the second section 4b. The first section 4a and the first fixed post 3a, when apart, form a first opening (not shown). The second section 4b and the second fixed post 3c and the third fixed post 3b, when apart, form a second opening (not shown) and a third opening (not shown).

The method for using the apparatus of FIGS. 4A, 4B and 4C involves setting the first section 4a having a small size length $L_1$ at the pivot point 6 and moving the swinging arm 4 until it touches against the smallest dimension of a particle 7 (not shown). Separate measurements are taken at the second section 4b having a large size length $L_2$, i.e., 3:1 and 5:1, thus determining if the longest dimension of the particle exceeds the 3:1 or 5:1 ratios. One particle is measured at a time.

The multiple ratios are compared at the same time as follows:

The smallest dimension of a particle on the short side of the pivot point 6 is set. The long side of the pivot point 6 has posts 3b and 3c to determine two ratios. Starting at the largest opening (5:1), the particle is brought towards the pivot point 6 until its largest dimension will not pass between the measuring points at a ratio. The particle is then classified as falling into one of the following groups: particles less than 3:1, particles between 3:1 and 5:1 and particles greater than 5:1.

Figure 5A:
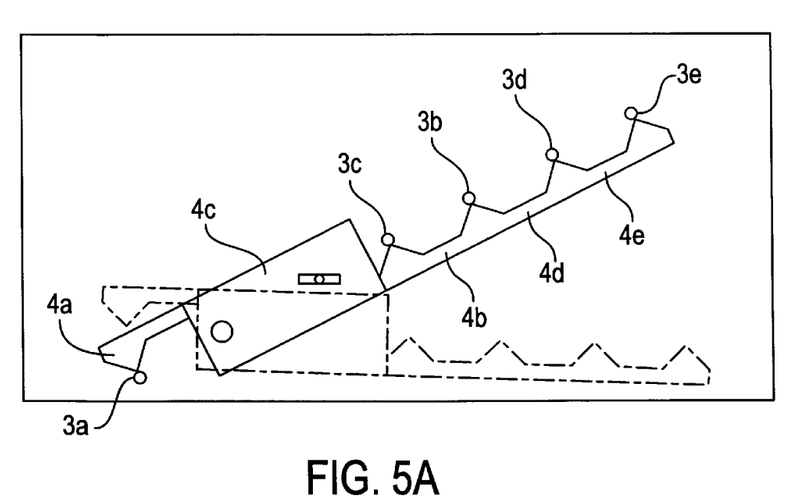
FIGS. 5A, 5B and 5C are schematics showing views of an apparatus for measuring the dimensions of particles in accordance with the present invention, wherein four measurements, i.e., 5:1, 4:1, 3:1 and 2:1, are carried out simultaneously.
Figure 5B:
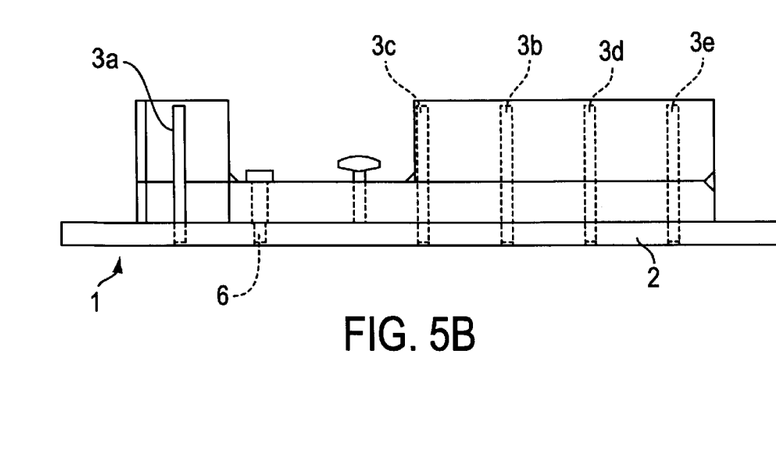
Figure 5C:
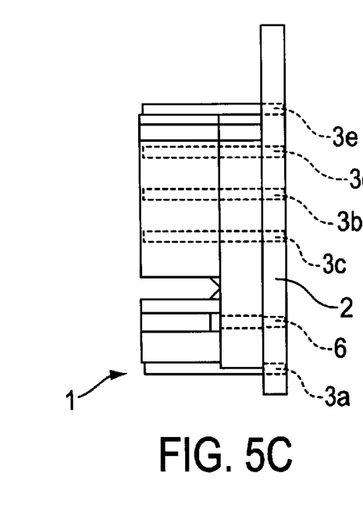
Figure 6:
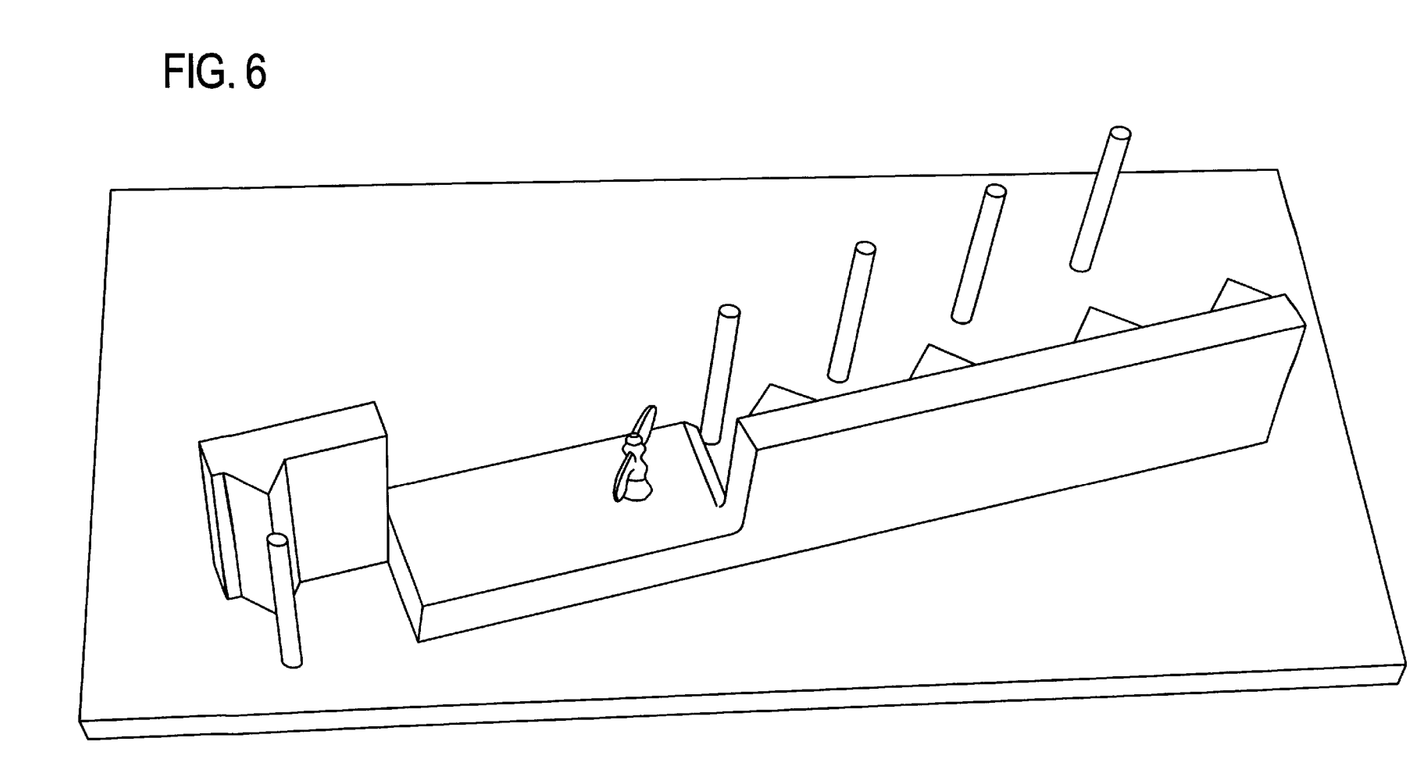
FIG. 6 shows an apparatus for measuring the dimensions of particles in accordance with the present invention, wherein 4 measurements, i.e., 5:1, 4:1, 3:1 and 2:1 may be carried out simultaneously.

Referring to FIGS. 5A, 5B and 5C, there is an apparatus for measuring the dimensions of particles in accordance with a second embodiment of the present invention. The apparatus shown in FIGS. 5A, 5B and 5C works similarly to the apparatus shown in FIGS. 4A, 4B and 4C. The difference between the apparatus in FIGS. 5A, 5B and 5C and the apparatus in FIGS. 4A, 4B And 4C being that the apparatus in FIGS. 5A, 5B and 5C has four ratio points, i.e., 2:1, 3:1, 4:1 and 5:1, as opposed to two ratio points, i.e., 3:1 and 5:1.

Thus, to compare multiple ratios at the same time: the smallest dimension of a particle on the short side of the pivot point 6 is set. The long side of the pivot point 6 has posts (3b, 3c, 3d, 3e) at the correct position to determine two, three, four, or five times the smallest dimension (ratio). Starting at the largest opening (5:1 position), the particle is brought towards the pivot point 6 until the particle's largest dimension will not pass between the measuring points at a ratio. The particle is then classified as falling into one of the following groups: particles less than 2:1, particles between 2:1 and 3:1, particles between 3:1 and 4:1, particles between 4:1 and 5:1, and particles greater than 5:1.

Referring again to FIGS. 5A, 5B and 5C, there is an apparatus for measuring the dimensions of particles in accordance with a second embodiment of the present invention. The apparatus contains a base plate 2 with five fixed posts, 3a, 3b, 3c, 3d and 3e and a swinging arm 4 mounted between the length of the first fixed post 3a and the fifth fixed post 3e. The swinging arm 4 is mounted on the base plate 2 so as to permit movement of the swinging arm 4 around a pivot point 6. The swinging arm 4 contains five sections, 4a, 4b, 4c, 4d and 4e. The first section 4a mates the first fixed post 3a. The second section 4b mates the second fixed post 3c and the third fixed post 3b. The first section 4a has a length $L_1$ that is less than the length $L_2$ of the second section 4b. The third section 4c connects the first section 4a and the second section 4b. The first section 4a and the first fixed post 3a, when apart, form a first opening (not shown). The second section 4b and the second fixed post 3c and the third fixed post 3b, when apart, form a second opening (not shown) and a third opening (not shown).

The fourth section 4d of length $L_3$ mates the third fixed post 3b and the fourth fixed post 3d. The fifth section 4e of length $L_4$ mates the fourth fixed post 3d and the fifth fixed post 3e.

The method for using the apparatus of FIGS. 5A, 5B and 5C involves setting the first section 4a having a small size length $L_1$ at the pivot point 6 and moving the swinging arm 4 until it touches against the smallest dimension of a particle 7 (not shown). Separate measurements are taken at the second section 4b, at the fourth section 4d and at the fifth section 4e, having larger size length $L_2$, $L_3$ and $L_4$, respectively, i.e., 2:1, 3:1, 4:1 and 5:1, thus determining if the longest dimension of the particle exceeds the 2:1, 3:1, 4:1 or 5:1 ratios. Starting at the largest opening (5:1), the particle is brought towards the pivot point 6 until its largest dimension will not pass between the measuring points at a ratio. The particle is then classified as falling into one of the following groups: particles less than 2:1, particles between 2:1 and 3:1, particles between 3:1 and 4:1, particles between 4:1 and 5:1, and particles greater than 5:1. One particle is measured at a time.

The present invention will now be further illustrated in the following non-limiting examples.

EXAMPLE

About 300,000 particles were measured using the apparatus and method of the present invention.

Representative samples of all course aggregate sizes used in asphalt pavement were collected from many states. Each sample was reduced with a mechanical splitter as if preparing to run a sieve analysis. A sieve is a wire cloth with uniform square openings of a specified dimension. Common sieve cloth sizes, designed to fit into mechanical shaking devices, are 8 in. round, 12 in. round, and large trays. The sieve cloth usually has a frame that keeps the cloth rigid during the separation process, and frames are stacked on top of each other (largest opening down to smallest). A sample is placed on the largest opening sieve and then agitated so that particles will fall to the lower sieves until the particle can't pass through and is "retained on" a sieve. After the agitation process (usually 10 minutes), the amount of particles retained on each of the stacked sieves is weighed to determine particle distribution. Many different sieve openings are commonly used to specify different aggregate products, with a range specified on critical sizes within the product. After reduction, the portion for testing was weighed:

| Size No. | Weight |
| --- | --- |
| 5, 57, 6, 67, 68 | 10,000 grams (minimum) |
| 7, 78, 789 | 5,000 grams (minimum) |
| 8, 89 | 4,000 grams (minimum). |

The samples were further reduced with a mechanical splitter only if within the sizes below until each fraction contained approximately 200 particles:

passing through 1½ in. and retained on 1 in.

passing through 1 in. and retained on ¾ in.

passing through ¾ in. and retained on ½ in.

passing through ½ in. and retained on ⅜ in.

passing through ⅜ in. and retained on no. 4 (close to ¼ in.)

passing through no. 8 (close to ⅛ in.)

(Regarding, no. 4 and no. 8, when a sieve size is preceded by no. or #, it means the number of square openings in a lineal inch. For example, a no. 4 means 4 square openings per inch by 4 square openings per inch (or 16 square openings per square inch). The openings are slightly smaller than ¼ inch because the wire strands that form each square reduces the amount of open area within the square.)

The samples were then tested with the apparatus and method of the invention. Each of the particles in each size fraction was tested against 5:1 and 3:1 ratios to determine the % flat and elongated particles at a 5:1 and a 3:1 ratio. After the particles were classified, the proportion of the sample in each group was determined by count and/or mass.

EXAMPLE

Figure 7:
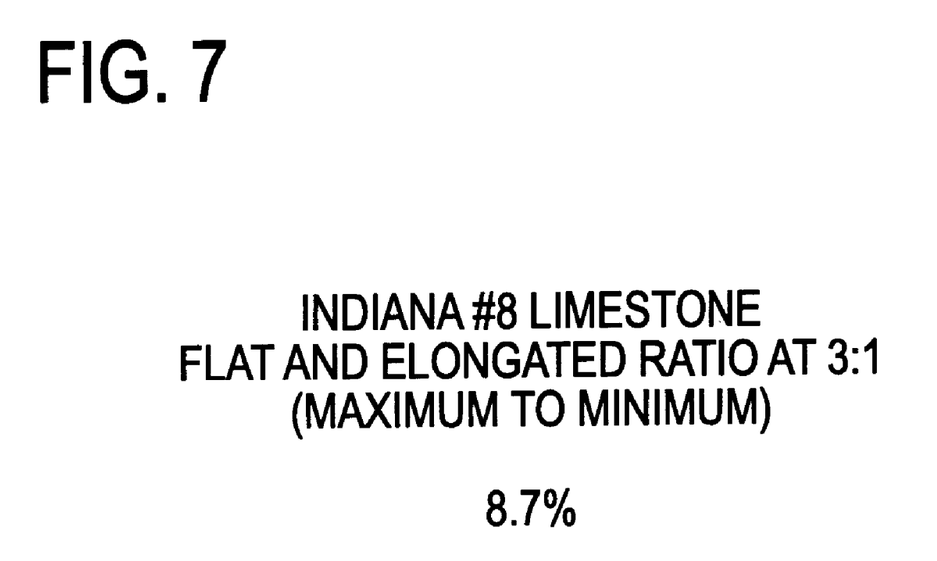
FIG. 7 shows the calculated results for Indiana #8 Limestone at 3:1, wherein the calculation is carried out according to conventional means, i.e., by determining the % of flat and elongated particles having a length to thickness (maximum to minimum) ratio greater than 3:1.
Figure 8:
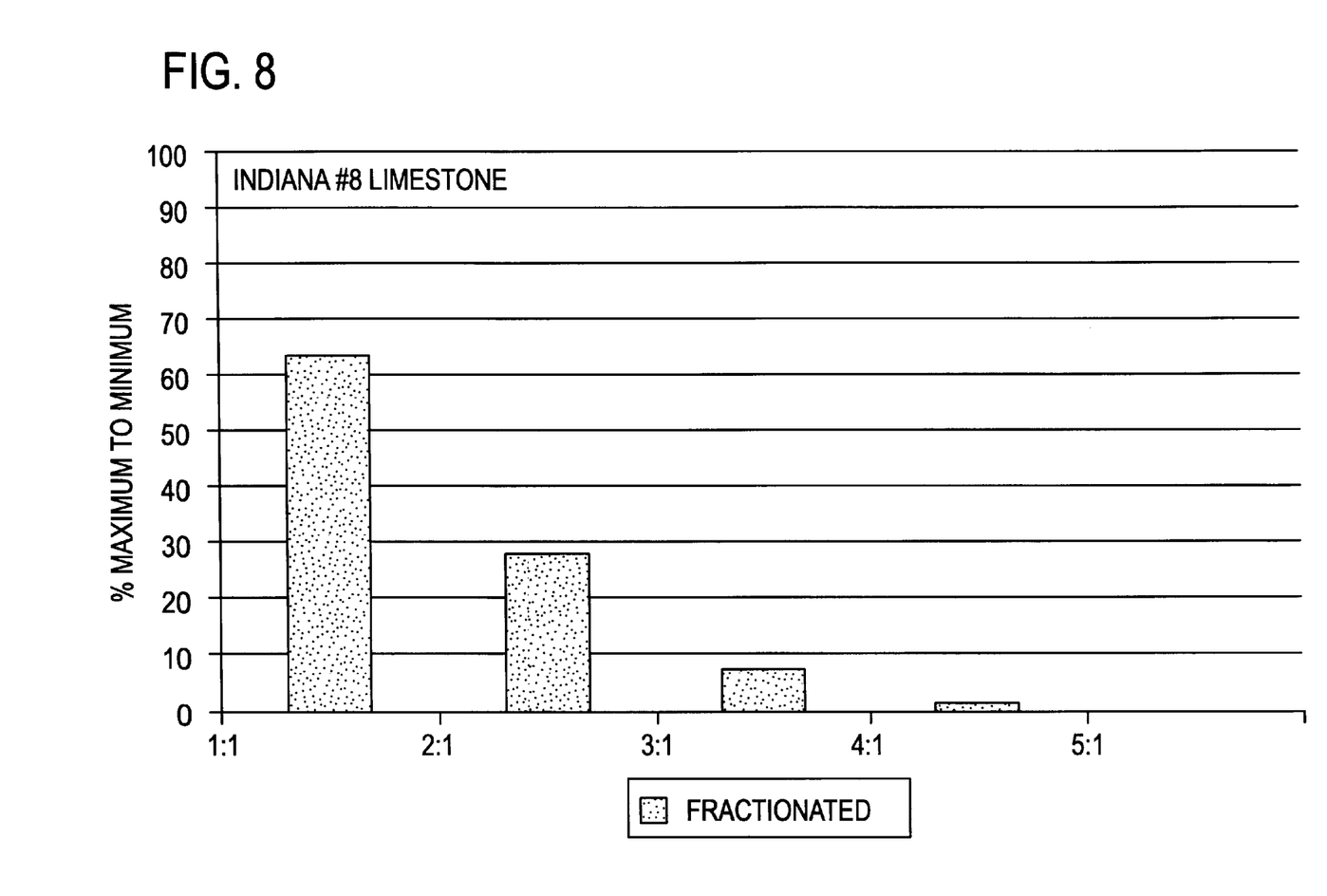
FIG. 8 is a bar graph showing the calculated results (calculated in accordance with the second embodiment of the invention) for the same sample of Indiana #8 Limestone as used in FIG. 7 at the following ratios: (a) between 1:1 and 2:1, (b) between 2:1 and 3:1, (c) between 3:1 and 4:1, and (d) between 4:1 and 5:1.
Figure 9:
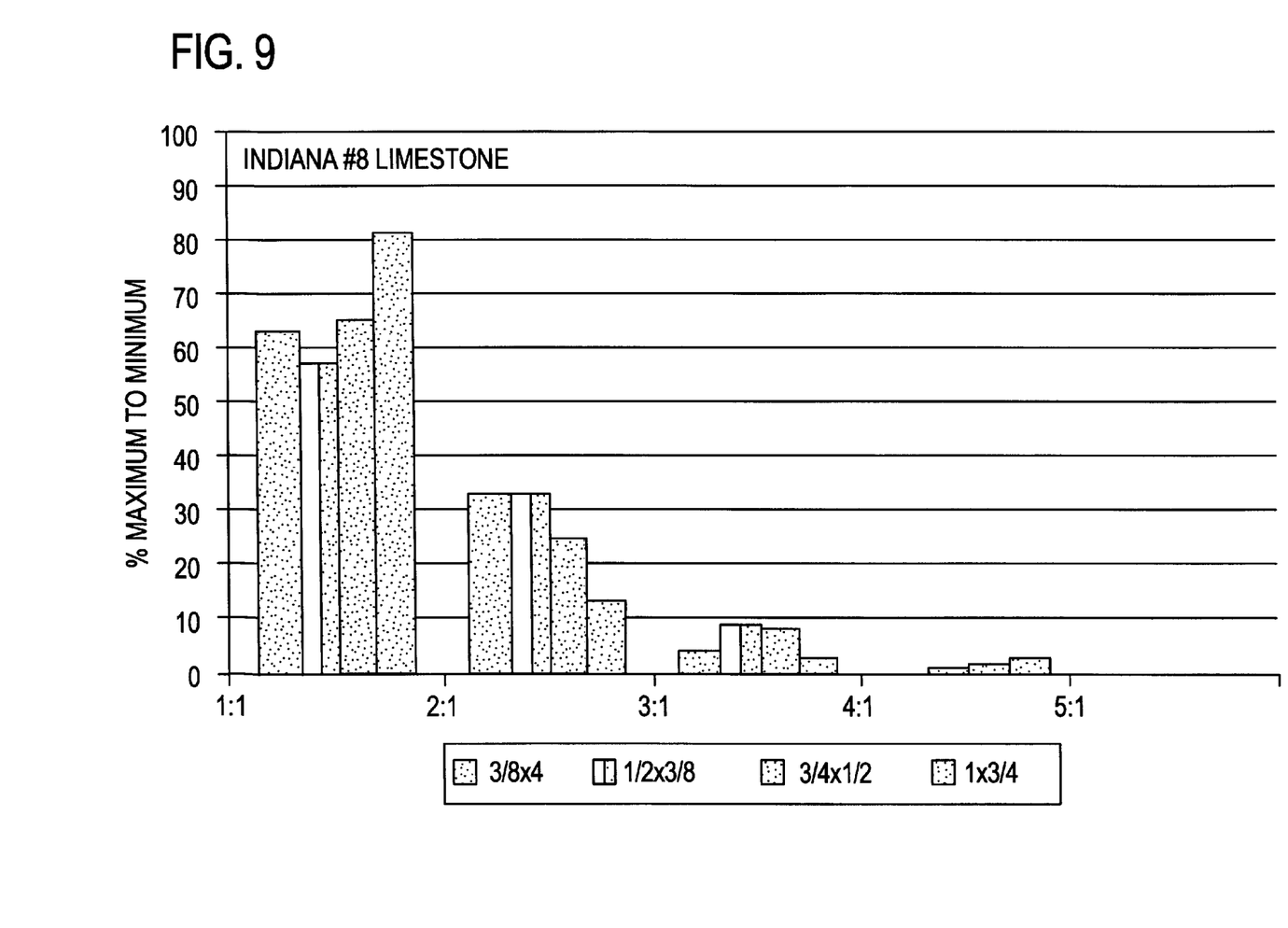

FIG. 7 shows the calculated results for Indiana #8 Limestone at 3:1, wherein the calculation is carried out according to conventional means, i.e., by determining the % of particles having a length to thickness (maximum to minimum) ratio greater than 3:1. As shown in FIG. 7, the percentage of particles having a width to thickness ratio greater than 3:1 is 8.7%. FIG. 8 is a bar graph showing the calculated results for the same sample of Indiana #8 Limestone as used in FIG. 7 calculated in accordance with the second embodiment of the invention, i.e., at the following ratios: (a) between 1:1 and 2:1, (b) between 2:1 and 3:1, (c) between 3:1 and 4:1, and (d) between 4:1 and 5:1. As shown in FIG. 8, additional information regarding the sample can be obtained by using the apparatus and method of the invention. FIG. 9 is a bar graph showing the calculated results (calculated in accordance with the second embodiment of the invention) for the same sample of Indiana #8 Limestone as used in FIG. 7 (and FIG. 8) at the following ratios: (a) between 1:1 and 2:1, (b) between 2:1 and 3:1, (c) between 3:1 and 4:1, and (d) between 4:1 and 5:1. FIG. 9 is similar to FIG. 8. However, the sample of Indiana #8 Limestone was further separated into the particle sizes shown in the box in FIG. 9, and then the apparatus of the invention was used to measure the different ratios found within each particle size group. FIG. 9 thus also shows the percent ratios found in each group of particle sizes found within the sample of Indiana #8 Limestone.

The invention has a fixed pivot point and once a minimum dimension has been determined; five different ratios may be determined at the other measured dimensions, at the same time; <2:1, 2:1, 3:1, 4:1, and 5:1. The invention allows a new characterization of particle shape to be determined, i.e., instead of describing a sample's particle shape with one number for a given ratio, the sample can be described by using up to five ratios.

The present invention reduces time and effort when measuring the dimensions of particles. The reduced time allows for more measurements to be made on the same particles. Thus, the invention provides a new way of classifying a product's particle shape.

Although the present invention has been fully described by way of examples with reference to the accompanying drawings, it is to be noted that various changes and modifications will be apparent to those skilled in the art. Unless the changes and modifications depart from the scope of the invention, they shall be construed as being included therein.

What is claimed is:

1. An apparatus for measuring dimensions of particles comprising:

a base;

three or more fixed posts mounted to said base;

a swinging arm pivotally mounted to said base about a pivot point wherein said swinging arm has a first section, wherein said first section mates with a first of the fixed posts, a second section wherein said second section mates with a second and third of the fixed posts, and a center section connecting said first section and said second section, wherein said first section has a length $L_1$ that is less than a length $L_2$ of said second section.

2. An apparatus for measuring dimensions of particles comprising:

a base;

at least three fixed posts mounted to said base; and a swinging arm pivotally mounted to said base about a pivot point and having:

a first section mated with one of said at least three fixed posts and having a first length, wherein a first opening is formed when said first section and said one of at least three fixed posts are not in contact;

a second section mated with a second and a third of said at least three fixed posts and having a second length that is greater than said first length, wherein second and third openings are formed when said second section does not contact said second and third fixed posts, wherein the second and third posts are positioned opposite the first post about the pivot point; and a third section connecting said first section and said second section.

3. An apparatus as claimed in claim 2, further comprising a fourth section extending from said second section and mating said second and a fourth of said at least three fixed posts, wherein a fourth opening is formed when said fourth section and said second and fourth posts are not in contact.

4. An apparatus as claimed in claim 3, further comprising a fifth section extending from said fourth section and mating said fourth and a fifth of said at least three fixed posts, wherein a fifth opening is formed when said fifth section and said fourth and fifth posts are not in contact.

* * * * *